US008984450B2

(12) United States Patent
Hu et al.

(10) Patent No.: US 8,984,450 B2
(45) Date of Patent: Mar. 17, 2015

(54) METHOD AND APPARATUS FOR EXTRACTING SYSTEMATIC DEFECTS

(71) Applicant: Taiwan Semiconductor Manufacturing Company, Ltd., Hsin-Chu (TW)

(72) Inventors: Jia-Rui Hu, Taichung (TW); Kai-Hsiung Chen, Danshuei Township (TW); Chih-Mihg Ke, Hsinchu (TW); Hua-Tai Lin, Hsinchu (TW); Tsai-Sheng Gau, HsinChu (TW)

(73) Assignee: Taiwan Semiconductor Manufacturing Company, Ltd., Hsin-Chu (TW)

( * ) Notice: Subject to any disclaimer, the term of this patent is extended or adjusted under 35 U.S.C. 154(b) by 0 days.

(21) Appl. No.: 14/180,822

(22) Filed: Feb. 14, 2014

(65) Prior Publication Data

US 2014/0282334 A1    Sep. 18, 2014

Related U.S. Application Data

(60) Provisional application No. 61/784,662, filed on Mar. 14, 2013.

(51) Int. Cl.
   *G06F 17/50* (2006.01)
(52) U.S. Cl.
   CPC .................................. *G06F 17/5081* (2013.01)
   USPC .......................................................... 716/52

(58) Field of Classification Search
   CPC .............................. G03F 1/144; G06F 17/5081
   USPC .......................................................... 716/52
   See application file for complete search history.

(56) References Cited

U.S. PATENT DOCUMENTS

| 7,729,529 | B2 | 6/2010 | Wu et al. | |
|---|---|---|---|---|
| 2012/0308112 | A1 | 12/2012 | Hu et al. | |
| 2014/0037188 | A1* | 2/2014 | Nakagaki et al. | 382/149 |
| 2014/0050389 | A1* | 2/2014 | Mahadevan et al. | 382/149 |
| 2014/0105482 | A1* | 4/2014 | Wu et al. | 382/149 |

* cited by examiner

*Primary Examiner* — Suresh Memula
(74) *Attorney, Agent, or Firm* — Haynes and Boone, LLP

(57) ABSTRACT

The present disclosure provides a method of systematic defect extraction. Primary and secondary areas are defined in a wafer layout. A plurality of defects is identified by a first wafer inspection for an outside-process-window wafer. Defects located in the secondary area are removed. Defects associated with non-critical semiconductor features are also removed via a grouping process. Sensitive regions are defined around defects associated with critical semiconductor features. A second inspection is then performed on the sensitive regions for an inside-process-window wafer, thereby identifying a plurality of potentially systematic defects. Thereafter, a Scanning Electron Microscopy (SEM) process is performed to determine whether the defects in the sensitive regions of the inside-process-window wafer are true systematic defects.

20 Claims, 11 Drawing Sheets

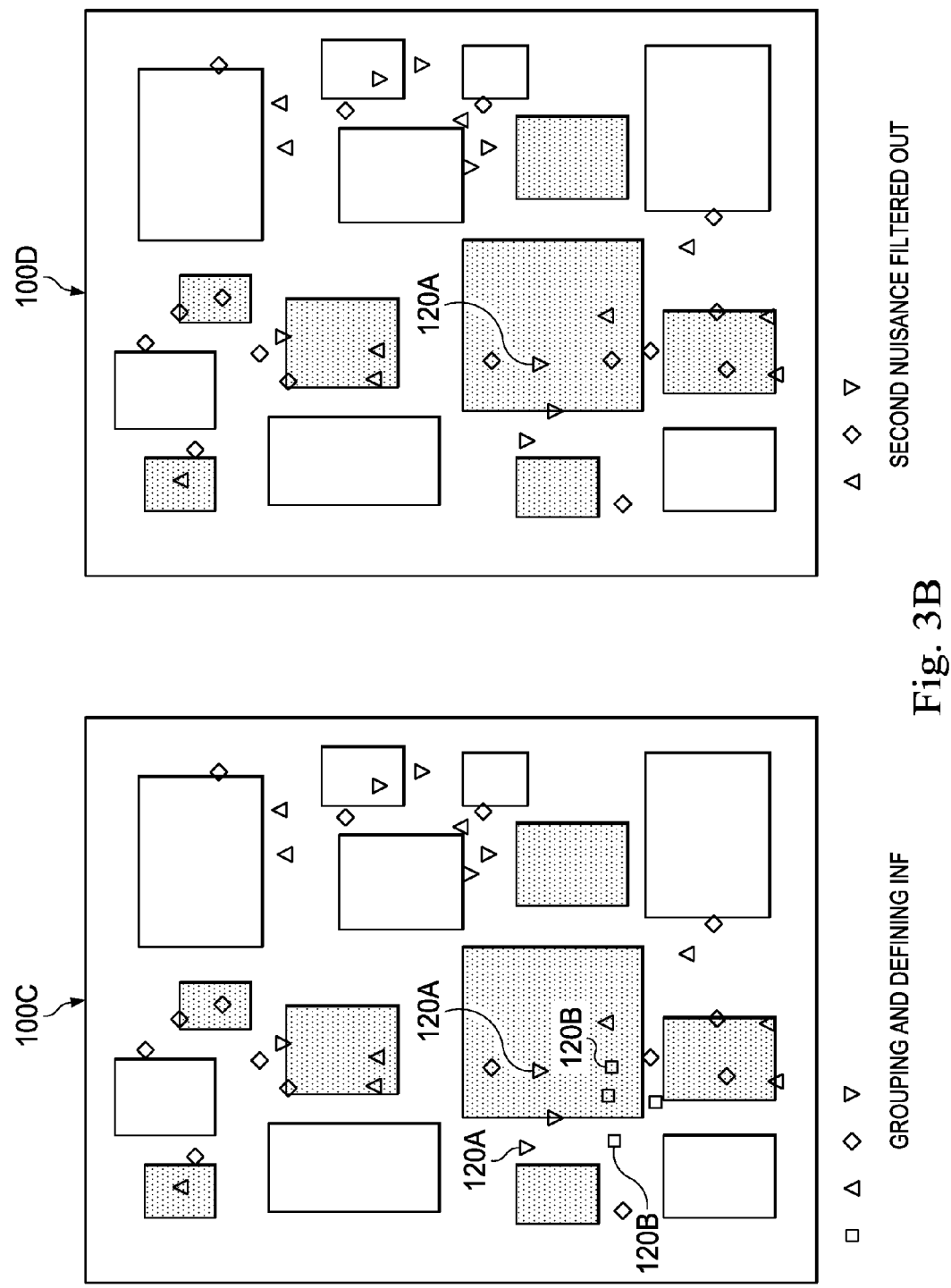

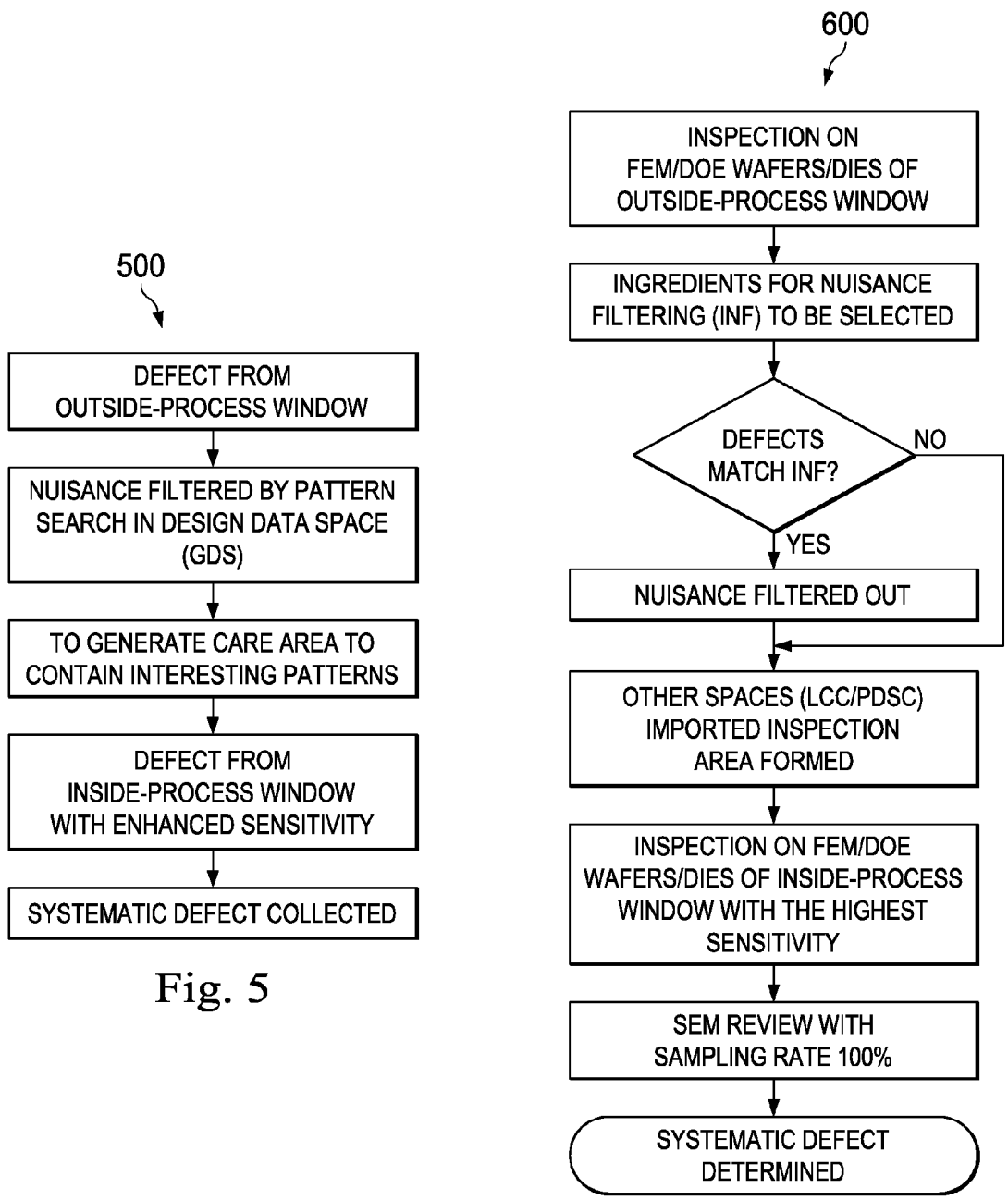

METHOD AND APPARATUS FOR EXTRACTING SYSTEMATIC DEFECTS

PRIORITY DATA

The present application is a utility patent application of U.S. provisional patent application No. 61/784,662, filed on Mar. 14, 2013, and entitled "Method and Apparatus for Extracting Systematic Defects", the disclosure of which is hereby incorporated by reference in its entirety.

BACKGROUND

The semiconductor integrated circuit (IC) industry has experienced rapid growth. Technological advances in IC materials and design have produced generations of ICs where each generation has smaller and more complex circuits than the previous generation. However, these advances have increased the complexity of processing and manufacturing ICs. In the course of integrated circuit evolution, functional density (i.e., the number of interconnected devices per chip area) has generally increased while geometry size (i.e., the smallest component that can be created using a fabrication process) has decreased. This scaling down process generally provides benefits by increasing production efficiency and lowering associated costs.

As a part of the IC fabrication process, wafers may undergo inspection to identify potential defects. Typically, such inspection may be done using an optical machine such as tools developed by KLA-Tencor. However, these inspections may identify a huge number of potential defects. To verify whether these potential defects are systematic defects, a scanning electron microscope (SEM) tool may be used. However, the SEM tools can only review a very small portion of the wafer at a time. In other words, the SEM review is a time-consuming process. Generally, it is simply not practical to do a full SEM review of a whole wafer. As a result, there is a risk that some systematic defects will not be caught.

Consequently, although existing techniques for identifying systematic defects on a wafer have been generally adequate for their intended purposes, they have not been entirely satisfactory in all respects.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

FIG. 5-8 are various flowcharts illustrating systematic defect extraction methods according to various aspects of the present disclosure.

DETAILED DESCRIPTION

Figure 1:
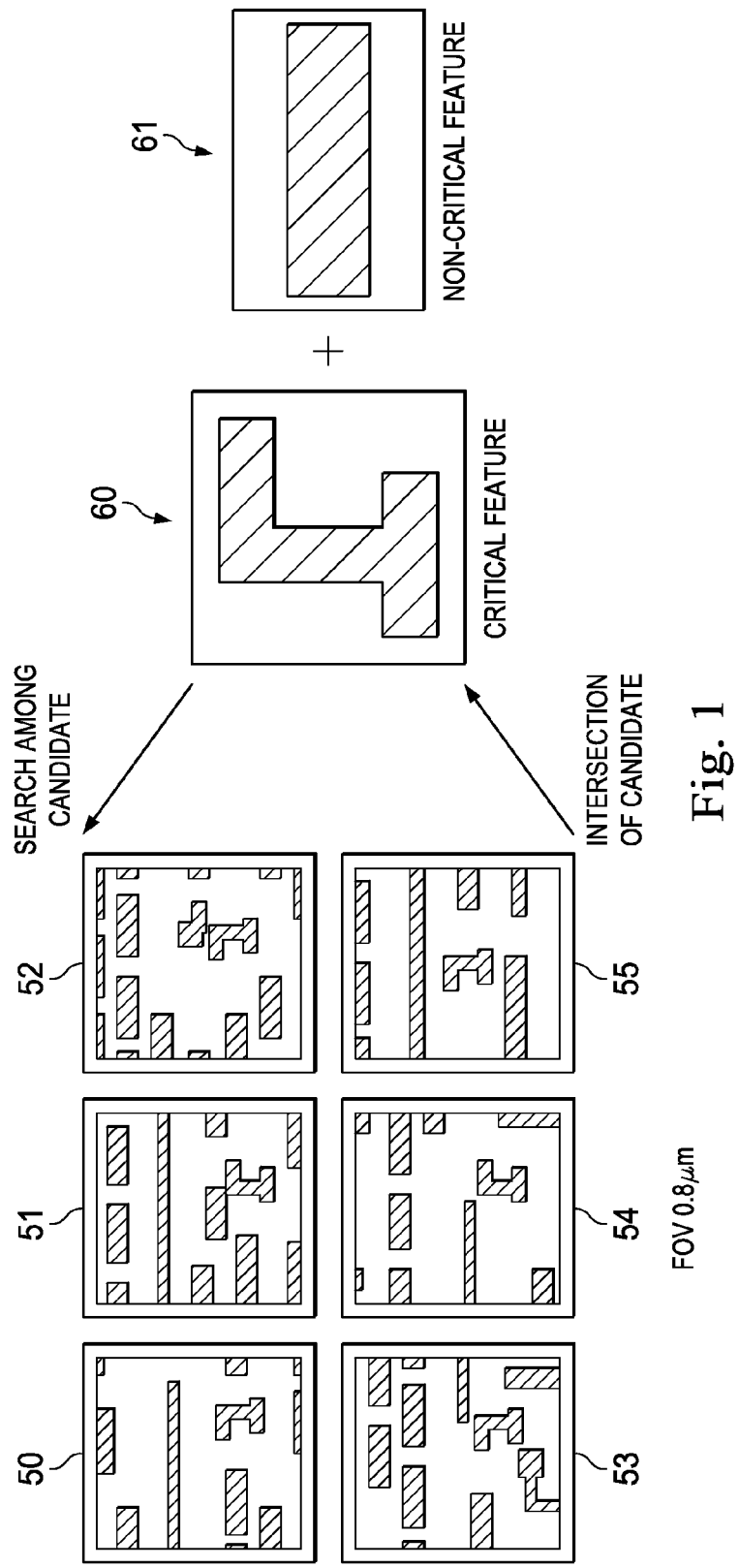
FIG. 1 is a diagram illustrating a grouping process according to various aspects of the present disclosure.

It is to be understood that the following disclosure provides many different embodiments, or examples, for implementing different features of the invention. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

As a part of the IC fabrication process, wafers may undergo inspection to identify potential defects. For a standard wafer inspection process, defects that are identified may include systematic defects, systematic random defects, and random or nuisance defects. Systematic defects and systematic random defects are often collectively referred to as a "hot spot." Such hot spots are typically caused by problems related to circuit design, mask design, or even by the implementation of optical proximity correction (OPC) features. These issues will likely manifest themselves in every wafer and/or chip. In other words, tuning fabrication process parameters will not reduce or eliminate systematic defects or systematic random defects. As such, it is important to identify the systematic defects or systematic random defects so that corrective actions may be taken to reduce or eliminate these defects from future wafers. For example, modifications may be made to the photomask or the circuit design.

On the other hand, random defects or nuisance defects may be attributed to a variety of factors such as unexpected/unforeseen fabrication process variations, contaminant particles, human errors, machine errors, etc. As such, the random defects or nuisance defects cannot be completely eliminated even if circuit or mask designs are optimized. Hence, it generally is not necessary to catch all the random or nuisance defects during wafer inspection, as their occurrence may be unrepeatable and random in nature. For reasons of simplicity, systematic defects and systematic random defects may be collectively referred to as systematic defects hereinafter, and random defects and nuisance defects may be collectively referred to as nuisance defects hereinafter.

In many cases, wafer inspection may be done using an optical machine, such as a machine developed by KLA-Tencor. Often times, the inspection involves performing quick optical scan to a reference die and a target die to generate a list of potential defects, which may be represented by signal irregularities as a result of the comparison. However, these inspections typically generate a huge number of potential defects. As discussed above, it is desirable to catch systematic defects while filtering out the random defects. To verify whether these potential defects are systematic defects, a scanning electron microscope (SEM) tool may be used. However, the SEM tools can only review a very small portion of the wafer at a time. Thus, the SEM review is a time-consuming process if all the potential defects generated by the inspection process need to be reviewed using SEM. Often times, it is simply not practical to do a full SEM review of the entire list of potential defects generated by the inspection. As a result, sometimes only a subset of all the potential defects is inspected using SEM, or only a representative portion of the wafer undergoes the inspection process to reduce the initial defect count. However, reviewing only a subset of the potential defects means that there is a risk that some systematic defects will not be caught, since these systematic defects may not be chosen to be examined by SEM or may manifest themselves only in uninspected portions of the wafer.

Another difficulty of systematic defect extraction relates to the sensitivity used in the inspection process. First, a high sensitivity in the inspection process needs to be used to fully collect the information needed to identify the raw defects (which may include both systematic defects and random defects). By the same token, a high sensitivity increases the raw defect count, meaning that there will be a large number of nuisance defects being caught. This is undesirable, since only systematic defects are of interest. Second, there might be a stage error from inspectors and SEM reviewers. To address the stage error issue, the size of field of view (FOV) of each defect must be sufficiently large, for example larger than about 2 microns (μm). But the larger FOV is more time consuming. Third, a pattern grouping process may need to be performed to reduce the number of patterns (and thus raw defects) of interest. However, due to this relatively large FOV (needed to address the stage error issue as discussed above), there may be a huge amount of patterns to undergo grouping, which again can be very time consuming. Furthermore, due to the large FOV, the environmental variation is increased within each FOV. This makes a pattern grouping more difficult. Thus, human loading errors may be more likely to occur and mistakes may be made in the process window analysis.

Thus, the bottleneck of systematic defection extraction and nuisance filtering is attributed to the fact that, in order to identify defects of interest (i.e., systematic defects), engineers have to review a large number (e.g., thousands or tens of thousands) of defects of interest by manual labor after inspection. This process is inefficient, time-consuming, and error-prone.

According to an aspect of the present disclosure, the cycle time of nuisance filtering is improved without quality loss by a novel method of pattern grouping and feature grouping. For example, common patterns and common features are extracted using an intersection method for candidate patterns, and then to be defined as critical or non-critical ones by a computerized analysis done by an hot spot analyzer tool, which is a separate machine than the wafer inspection tool in the present embodiment. In some embodiments, the hot spot analyzer tool is a NanoScope™ Hotspot Pattern Analyzer (HPA) made by Anchor Semiconductor™. The grouping process of the present disclosure allows raw defect count to be reduced and nuisance defects to be filtered out, as discussed in more detail below.

An example grouping scheme is illustrated in FIG. 1. In FIG. 1, an FOV of 0.8 μm is used, which is smaller than the 2.0 μm FOV often required by traditional processes. The top views of six FOVs 50-55 are illustrated in FIG. 1. Each of the FOVs 50-55 corresponds to a respective pattern group, which and includes a plurality of features. In other words, the six FOVs cannot be grouped together, since they each contain different layout characteristics. Only FOVs that include substantially layout characteristics may be grouped together as a common FOV (or a common pattern group). This is referred to as pattern grouping. In other words, to generate the six FOVBs 50-55 shown in FIG. 1, a pattern grouping process has already been performed.

The features in each FOV manifest themselves as having different geometric shapes. By way of an "intersection method," which may include one or more computerized feature extraction and comparison analyses, common features from the six FOVs 50-55 are identified. For example, the common features are features that repeat themselves (even if oriented differently) in two or more FOVs 50-55. Based on the geometric shapes of these common features, it can be determined whether a particular common feature is a critical feature, such as a critical feature 60, or merely a non-critical feature, such as a dummy feature 61. This is referred to as feature grouping.

A set of rules may be applied to help determine whether a common feature is a critical feature. For example, these rules may examine whether a width (or any specific dimension) of a feature is too small (i.e., below a predefined threshold), or whether the feature contains a corner, etc. Different sets of rules may apply in different embodiments. Once an "intersection" of the different FOVs 50-55 (i.e., different pattern groups) yield a common critical feature, these different pattern groups or FOVs may be grouped into one, thereby substantially reducing the number of defects of interest that need to be identified. In addition, after the critical features (such as the critical feature 60) are determined, they will be relevant and used for the subsequent analyses discussed below. Meanwhile, the non-critical features may be filtered out later in a nuisance defect filtering process.

The present disclosure also segregates layout regions of a wafer into primary areas and secondary areas. In some embodiments, primary and secondary areas are defined where there are narrower process windows relative to other inspection areas. Other areas outside the primary and secondary areas are defined as areas that are subject to higher nuisance rate if the same sensitivity with primary inspection area is applied.

Figure 2:
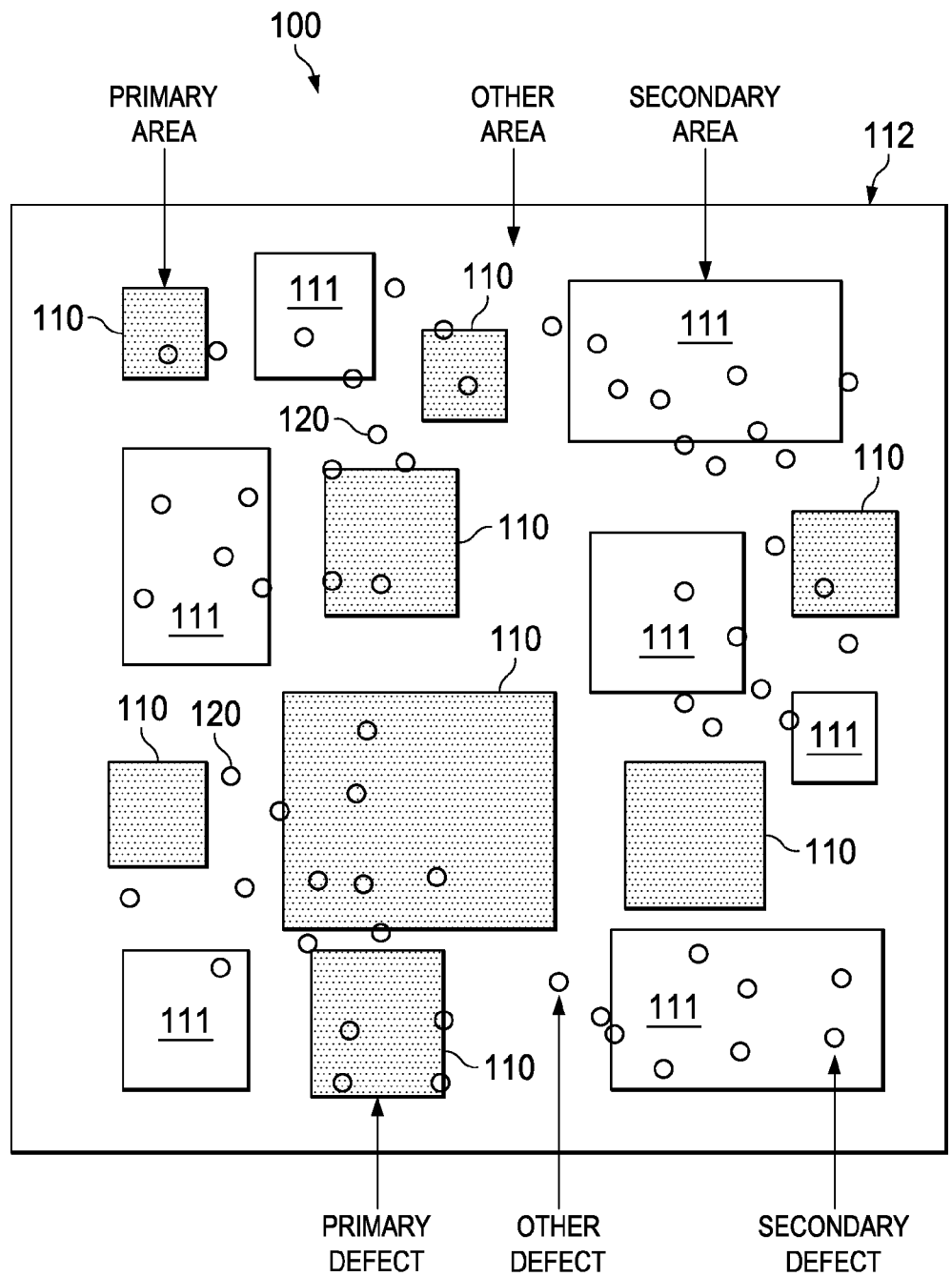
FIG. 2 is a diagram illustrating an example area of a wafer containing primary and secondary areas and defects according to various aspects of the present disclosure.

FIG. 2 provides an example of defining primary and secondary areas. A portion of a chip layout 100 (top view) is shown in FIG. 2. There are many different ways to define primary and secondary areas in a chip layout, one of which is defining primary and secondary areas based on the importance or criticality of a particular area of a layout. In FIG. 2, primary areas 110 are defined as areas of the highest criticality in the layout (for example areas that have to narrower process windows), secondary areas 111 are defined as areas low or no criticality in the layout, and other areas 112 are defined as the rest of the chip areas outside either the primary areas 110 or the secondary areas 111.

A plurality of example defects such as defects 120 are also shown in FIG. 2. The defects 120 are generated by comparison with a reference die as a part of an inspection process. The defects are illustrated as dots for reasons of simplicity, but it is understood that each defect may represent any type of abnormality, including but not limited to undesired shorting/opening, excessive roughness, contaminants, etc. To determine which defects need to be kept for subsequent analysis, the defects located in the primary areas 110 are given priority, since the primary areas 110 are identified as the areas of the highest criticality. An increased sensitivity may be applied to the defects in the primary areas 110.

Figure 3A:
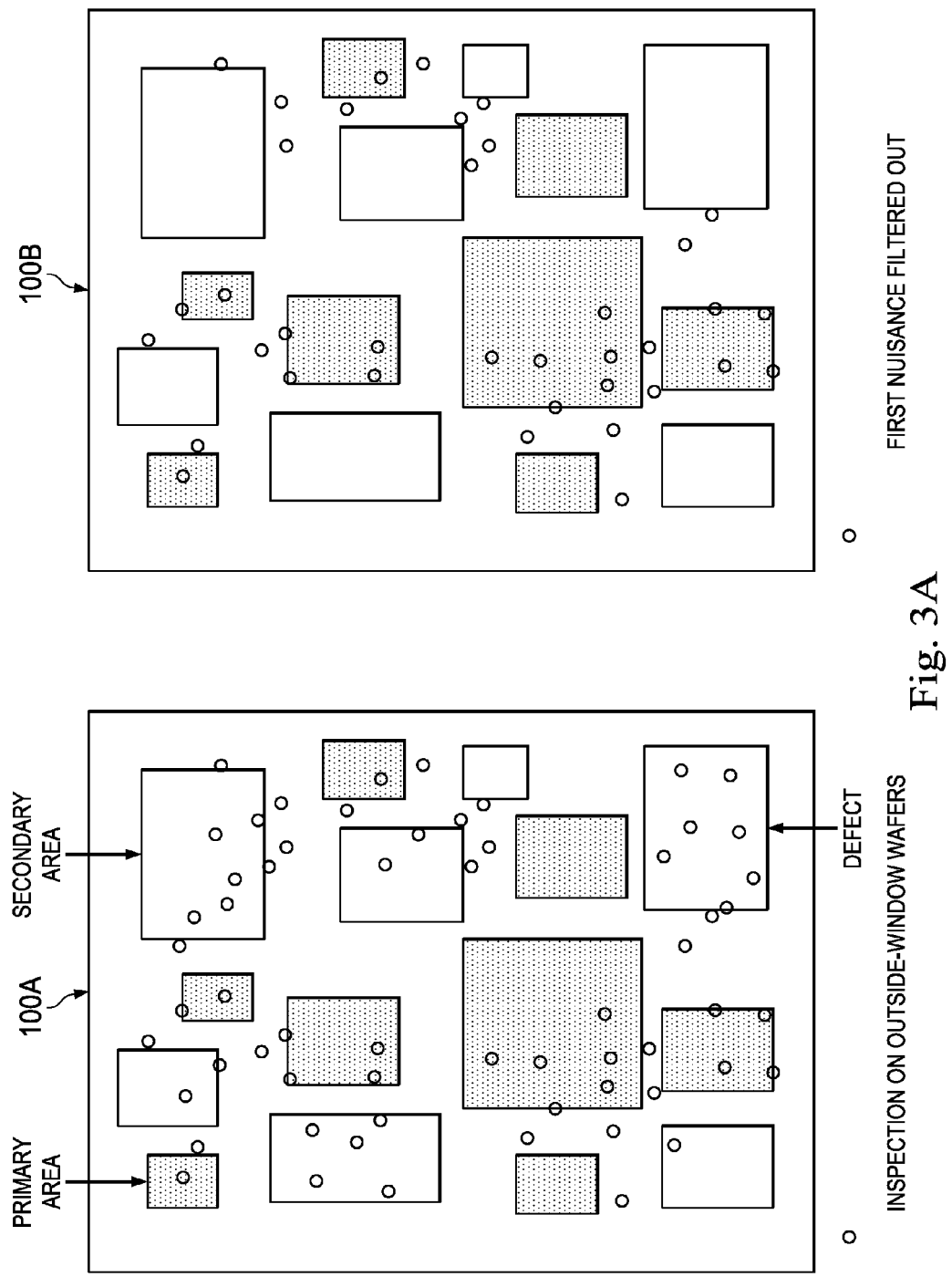
FIGS. 3 and 4 are diagrams illustrating two different embodiments of performing a systematic defect extraction method according to various aspects of the present disclosure.
Figure 3C:
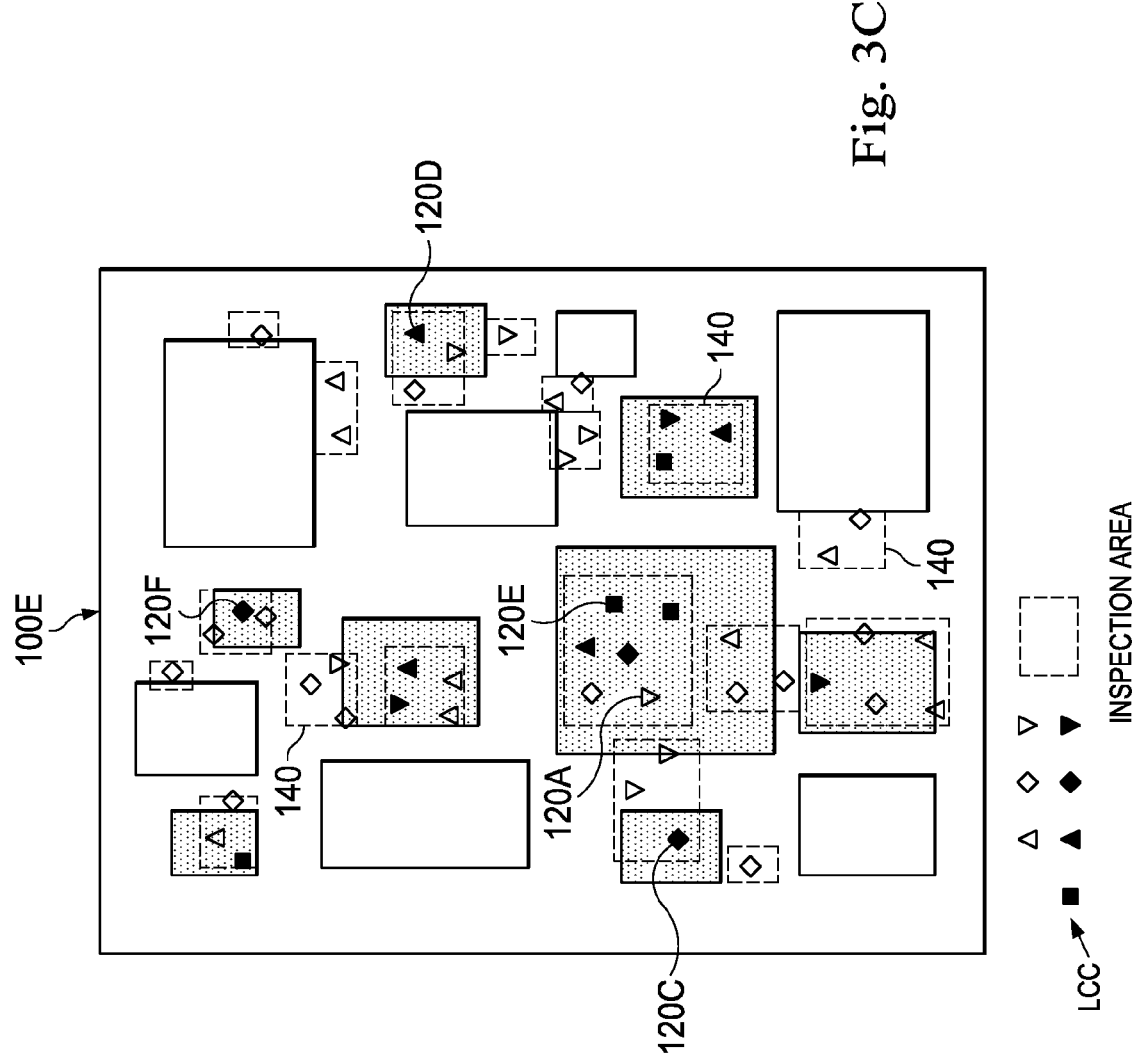
Figure 3D:
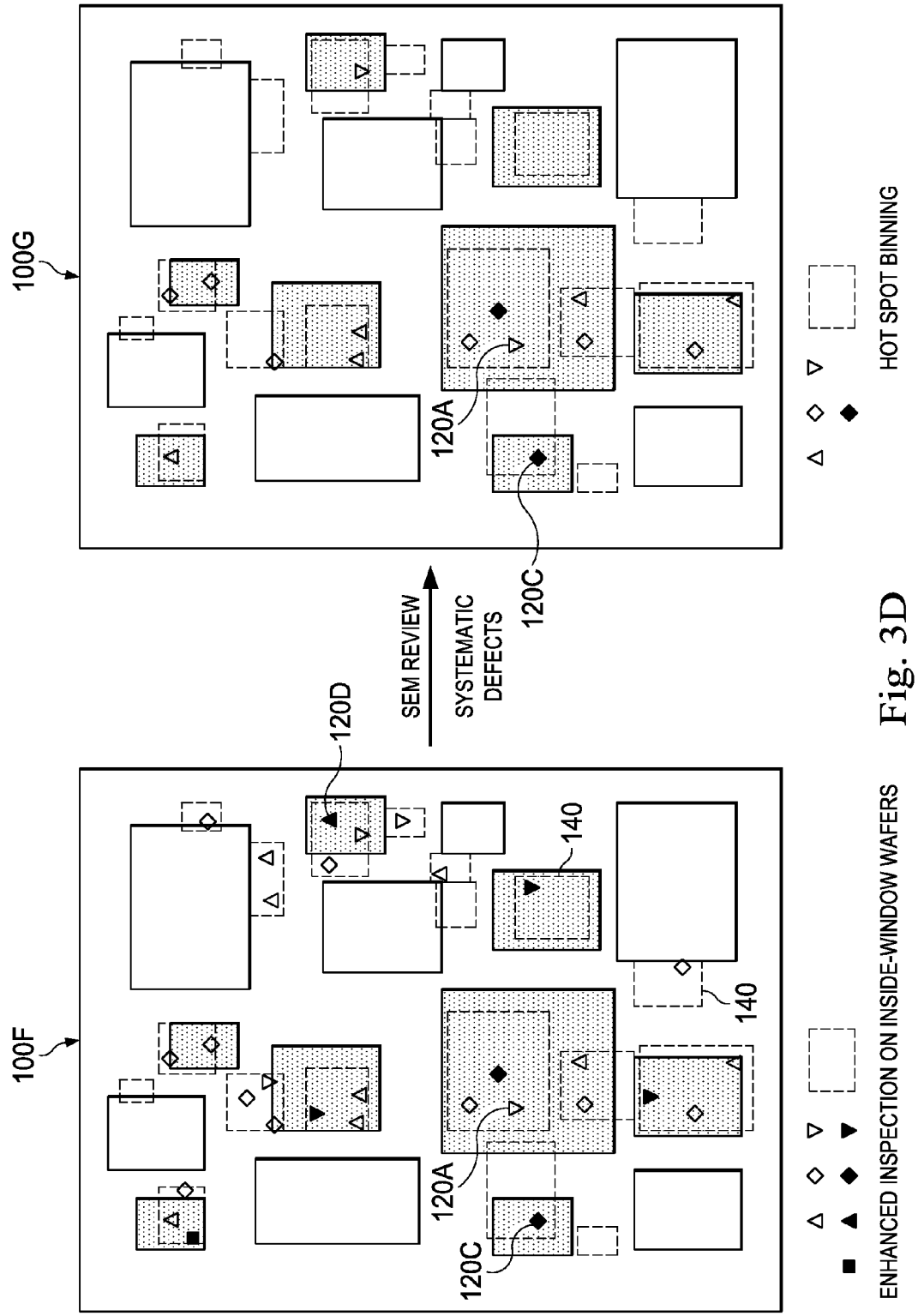
Figure 4:
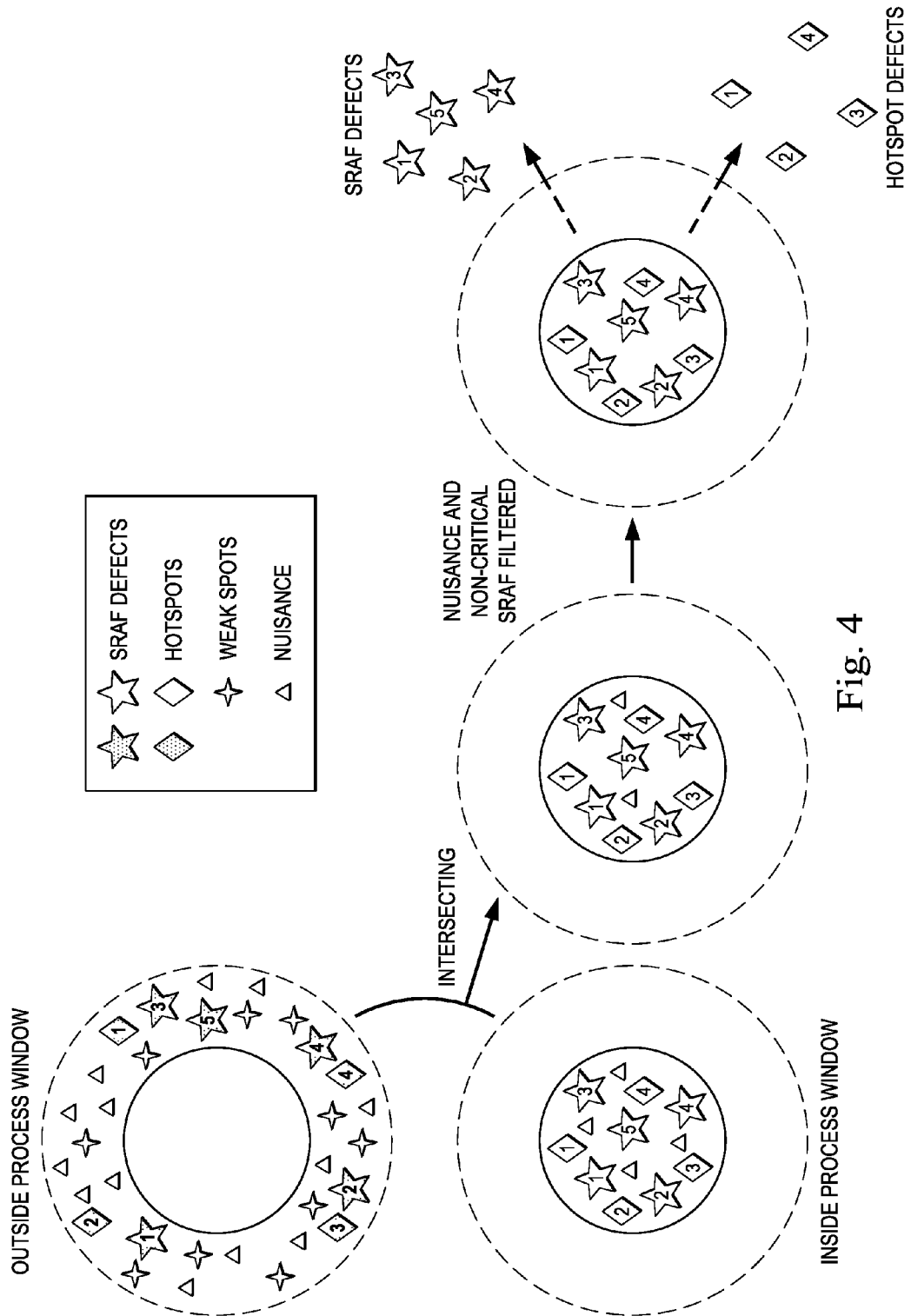

FIGS. 3 and 4 illustrate two embodiments of defect-filtering according to the present disclosure. A first embodiment of defect-filtering is shown in FIG. 3. In more detail, FIG. 3 illustrates a plurality of layouts 100A-100G, each one corresponding to a different stage or step of the defect-filtering process. The primary areas 110, secondary areas 111, and other areas 112 are the same for the layouts 100A-100G (i.e., same as those shown in FIG. 2) and are not specifically labeled in FIG. 3 for reasons of simplicity. Similarly, many of the various defects appearing in FIG. 3 are not specifically labeled either for reasons of simplicity.

The layout 100A contains all the defects shown in FIG. 2 that are identified using an inspection process. In other words, the defects in the layout 100A are identified via the comparison process with a reference die using a reduced sensitivity. Note that the inspection is done for an outside-process-window wafer. It is understood that the term "wafer" herein may refer to an entire wafer, a portion of the entire wafer, or a chip on the wafer. Next, as discussed above, the secondary areas are defined as areas of low or no criticality. Thus, the defects located in the secondary areas are considered nuisance defects and are filtered out. As such, the defects in the secondary areas no longer appear in the layout 100B.

Thereafter, a pattern grouping process is performed to the layout 100C, specifically to the primary areas 110 and the other areas 112. The grouping process is done using an analyzer machine that is separate from the SEM tool used to perform wafer inspection as discussed above. The grouping process is performed such that FOVs that are substantially identical to other FOVs are grouped together. The FOVs cannot be illustrated in FIG. 3 due to their tiny sizes. The defects belonging to the common FOVs that are grouped together are illustrated the same in FIG. 3. For example, the defects belong to commonly grouped FOVs may be color-coded the same, such as defects 120A that belong to a common FOV1, or defects 120B that belong to a different common FOV2, wherein FOV1 and FOV2 have different patterns.

A feature grouping process is also performed. The feature grouping process may be similar to the grouping process shown in FIG. 1. In other words, similar critical features from different FOVs are identified, and similar non-critical features from different FOVs are also identified. In some embodiments, the feature grouping process includes an ingredient nuisance filtering (INF) process. The overlap of the pattern grouping process and the feature grouping process may be a non-limiting example of the "intersection" method discussed above. As shown in the layout 100D, the defects 120B (from all commonly-grouped FOVs) associated with the non-critical features are filtered out (i.e., removed), thereby further reducing the defect count. Since these filtered-out defects 120B are associated with non-critical features, they may also be considered examples of nuisance defects.

The defects that still remain (as shown in the layout 100D) after these nuisance defects are filtered out are defects that deserve further scrutiny. Referring to the layout 100E, localized regions are drawn around the remaining defects. These localized regions are represented by boxes such as boxes 140. Recall from previous discussions that the sensitivity of inspection has been set to be relatively low so far, because a high sensitivity will let in an extremely high number of defects, thereby making defect identification impractical. Thus, a relatively low sensitivity has been used up to this point. In some embodiments, the low sensitivity corresponds to less than 1,000,000 defects per wafer. However, the defects are not very clear due to the low sensitivity, and not all the defects may necessarily be caught due to the low sensitivity. Thus, at the step corresponding to the layout 100E, an inspection is done for only those localized regions designated by the boxes (such as the boxes 140). The inspection is done at a greater sensitivity. In some embodiments, this enhanced sensitivity corresponds to more than 1,000,000 defects per wafer, if no localized regions. This higher-sensitivity inspection is more practical since it is done not for the whole wafer, but only for selected regions of the wafer, namely the regions of the wafer where the important defects appear. As a result of the higher-sensitivity inspection, more defects such as defects 120C-120F (represented by triangles in the layout 100E) that were previously unidentified are caught.

Note that the higher-sensitivity inspection for the layout 100E is still done for outside-process-window wafers. Referring now to the layout 100F, an enhanced inspection is done for inside-process-window wafers. Theoretically, inside-process-window wafers are not supposed to have defects. Nevertheless, some of the defects such as 120A, 120C, or 120D still remain even for the inside-process-window wafer layout 100F. These defects may qualify as potential systematic defects and need further investigation. Meanwhile, some of the other defects such as defects 120E and 120F appear in the outside-process-window wafer (layout 100E) but not in the inside-process-window wafer (100F). These defects may be considered nuisance defects and may be filtered out. Thus, according to the present disclosure, the outside-process-window wafer is used to determine which localized regions of the wafer deserve more attention and further investigation. These localized regions are the problem areas on any wafer. Thereafter, an inside-process-window wafer is examined in detail specifically for these problem areas. Again, in FIG. 3, these problem areas are illustrated as the boxes such as the boxes 140.

As discussed above, the inspection processes discussed above involve performing an optical scan of a target chip and comparing the scan results with a reference chip. The "defects" caught by the inspection correspond to irregularities based on the scan result. These irregularities may or may not reflect actual defects. To accurately determine which of these irregularities are actually defects, an SEM process is performed. A SEM process involves using an electron microscope to produce images of a sample by scanning the sample with a focused beam of electrons. In other words, an SEM process can be used to take a very detailed picture of a sample. The detailed image captured by the SEM process allows true defects to be ascertained. However, a drawback of SEM processes is that they are very time-consuming. Thus, it is impractical to perform an SEM process to an entire wafer. Here, the SEM process is only performed to the selected regions of the wafer corresponding to the defects that still remain in the layout 100F. Recall that the defects that still remain in the layout 100F are potentially systematic defects. Hence, they deserve the time-consuming scrutiny required by the SEM process. A detailed picture can be taken for each of these potentially systematic defects to further evaluate whether or not they are indeed defects.

As a result of the SEM process, some of the defects such as defects 120D are filtered out again as nuisance defects, while other defects such as the defects 120C and 120A still remain. These remaining defects shown in the layout 100G are deemed to be the true systematic defects. These are the defects that need to be addressed, for example by changing the mask or circuit design. Otherwise, the defects are likely to appear on every future wafer. These systematic defects may also be binned in accordance with their specific characteristics, and this is referred to as hot spot binning.

FIG. 4 illustrates an alternative embodiment of defect-filtering according to various aspects of the present disclosure. The defects shown in FIG. 4 include sub-resolution assist feature (SRAF) defects, hot spot defects, weak spot defects, and nuisance defects, each of which is represented by a different symbol. First, a defect analysis is performed on an outside-process-window wafer as well as an inside-process-window wafer. A lower sensitivity is used for the outside-process-window wafer, and a higher sensitivity is used for the inside-process-window wafer. Different types of defects may be identified for each of the outside-process-window wafer and the inside-process-window wafer. Thereafter, an intersection process of them is performed. If an outside-processwindow wafer contains a defect that is not found in the inside-process-window wafer, then that defect is considered to be a weak spot. If an inside-process-window wafer contains a defect that is not found in the outside-process-window wafer, then that defect is considered to be a nuisance defect. The intersection process filters out the weak spots and the nuisance defects, thereby leaving only the hot spots (systematic defects) and the SRAF defects. If only the hot spots are desired, then the SRAF defects may be removed as well.

FIG. 5 is a flowchart illustrating a method 500 of systematic defect extraction according to the various aspects of the present disclosure. According to the method 500, the defects from outside-process-window wafers are identified. This is done using a lower sensitivity. The nuisance defects among these defects are then filtered by pattern search in a design data space (GDS). Afterwards, the method 500 involves generating a care area that contains interesting patterns (or patterns of interest). Thereafter, the defects from inside-process window are identified with a higher sensitivity inspection. Thereafter, systematic defects are collected.

FIG. 6 is a flowchart illustrating a method 600 of systematic defect extraction according to the various aspects of the present disclosure. According to the method 600, an inspection on FEM/DOE wafers/dies of outside-process window is done. Then, ingredients for nuisance filtering (INF) are selected. The method 600 then involves a decision step to determine whether the defects match INF. If yes, the nuisance defects are filtered out, and then other spaces (LCC/PDSC) imported inspection area is formed. If the answer from the decision step is no, then the method 600 jumps to a different step, where inspection is done on FEM/DOE wafers/dies of inside-process window within the highest sensitivity. Thereafter, SEM review is done with a sampling rate of 100%. Thereafter, systematic defects are determined.

Figure 7:
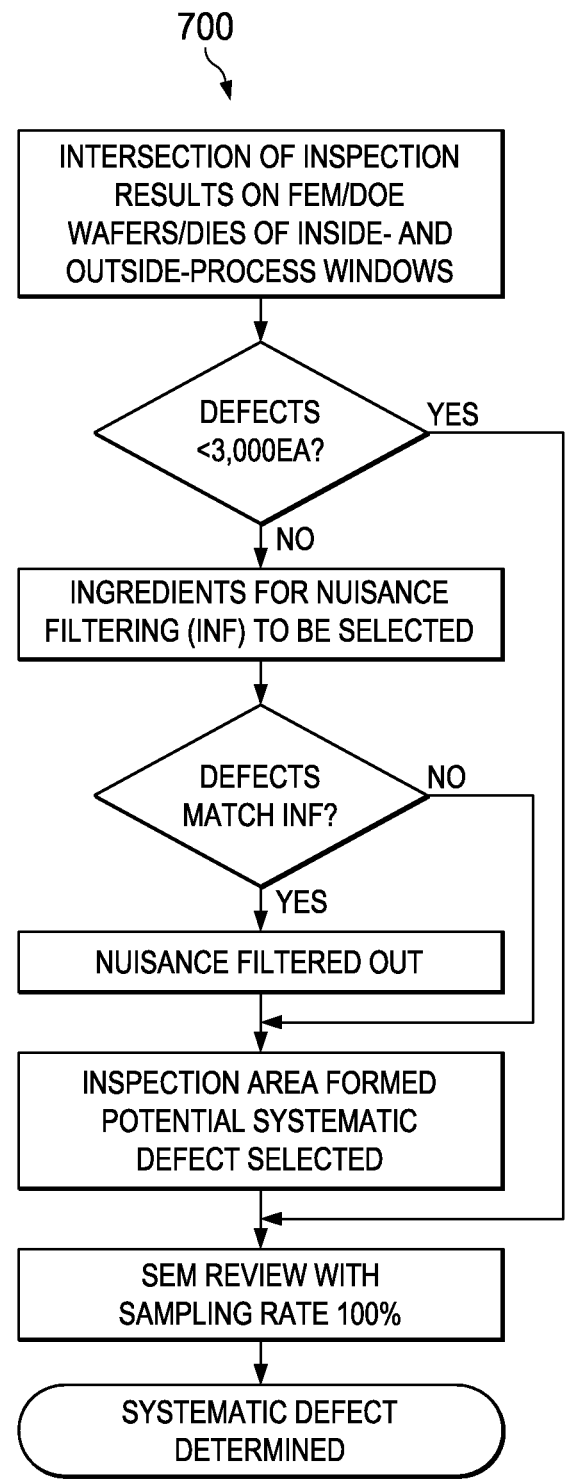

FIG. 7 is a flowchart illustrating another method 700 of systematic defect extraction according to the various aspects of the present disclosure. According to the method 700, an intersection of inspection results on FEM/DOE wafers/dies of inside and outside-process windows is done. The method 700 then involves a decision step to determine whether less than 3000 defects are present. If yes, the method 700 jumps to SEM review with a 100% sampling rate. If not, the method first goes to a step where ingredients for nuisance filtering (INF) is selected. If the defects match INF, then the method 700 filters out nuisance defects. Inspection area formed potentially systematic defects are then selected. If the defects don't match INF, the step jumps to the step of selecting inspection formed potentially systematic defects directly. Thereafter, the method goes to a SEM review with a sampling rate of 100%. Thereafter, systematic defects are determined.

Therefore, according to the various aspects of the present disclosure, at least the following aspects are novel.
1. A new flow to extract systematic and SRAF defects
2. To use pattern search to look for nuisance in GDS including main, dummy, and SRAF patterns
3. To use feature grouping to reduce the number of samples
4. To separate nuisance features from critical ones after feature grouping
5. To link with metrology tools
6. To detect systematic and SRAF defects on two different FEM/DOE pattern wafers/dies of outside-process window and inside-process window with normal and higher inspection sensitivity, respectively.

The systematic defect extraction method of the present disclosure may include, but is not limited to, one or more of the following features:

As many raw defect counts of FEM/DOE wafers as possible for data input

Faster and more accurate processes of nuisance filtering

Precise definition of inspection area to cover every possible systematic defect

It allows inspection of FEM/DOE wafers/dies inside-process windows with the highest sensitivity than that used for outside-process windows.

Greatly-reduced final defect count for the extraction of systematic defect.

Flexible to combine other data spaces (e.g., LCC/PDSC).

Self-examination of inspection area with well-known systematic defect

Figure 8:
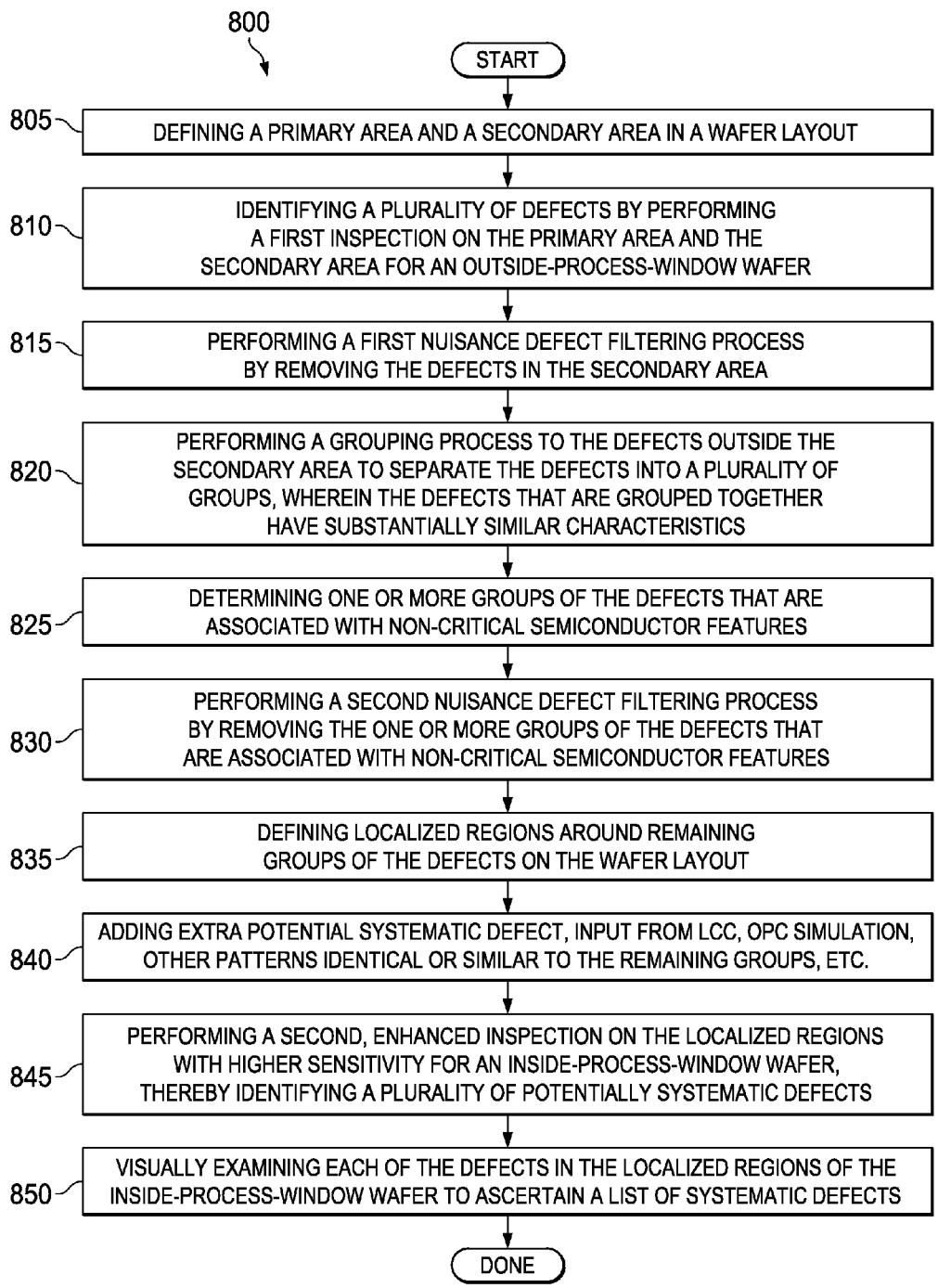

FIG. 8 is a flowchart illustrating another method 800 of systematic defect extraction according to the various aspects of the present disclosure. The method 800 includes a step 805 of defining a primary area and a secondary area in a wafer layout. The method 800 includes a step 810 of identifying a plurality of defects by performing a first inspection on the primary area and the secondary area for an outside-process-window wafer. The method 800 includes a step 815 of performing a first nuisance defect filtering process by removing the defects in the secondary area. The method 800 includes a step 820 of performing a grouping process to the defects outside the secondary area to separate the defects into a plurality of groups, wherein the defects that are grouped together have substantially similar characteristics. The method 800 includes a step 825 of determining one or more groups of the defects that are associated with non-critical semiconductor features. The method 800 includes a step 830 of performing a second nuisance defect filtering process by removing the one or more groups of the defects that are associated with non-critical semiconductor features. The method 800 includes a step 835 of defining localized regions around remaining groups of the defects on the wafer layout. The method 800 includes a step 840 of adding extra potential systematic defect, input from LCC, OPC simulation, other patterns identical or similar to the remaining groups, etc. The method 800 includes a step 845 of performing a second enhanced, inspection the localized regions with higher sensitivity for an inside-process-window wafer, thereby identifying a plurality of potentially systematic defects. The method 800 includes a step 850 of visually examining each of the defects in the localized regions of the inside-process-window wafer to ascertain a list of systematic defects.

Figure 9:
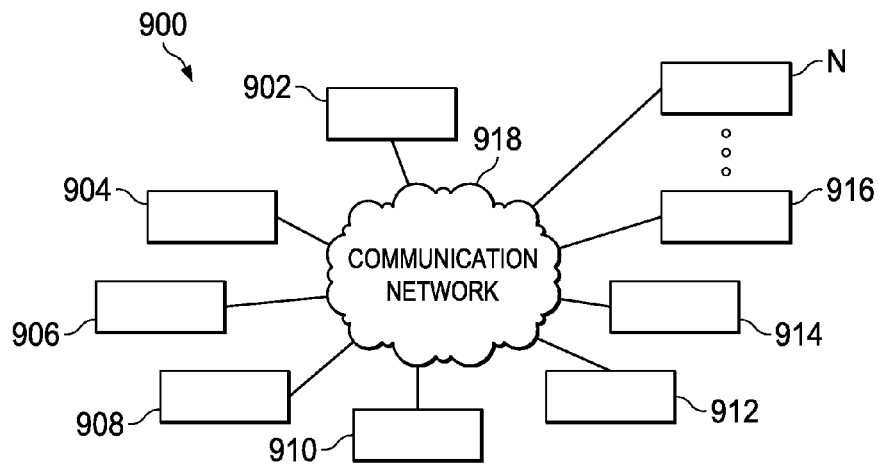
FIG. 9 illustrates an integrated circuit fabrication system according to various aspects of the present disclosure.

FIG. 9 illustrates an integrated circuit fabrication system 900 for performing the various aspects of the present disclosure. The fabrication system 900 includes a plurality of entities 902, 904, 906, 908, 910, 912, 914, 916 . . . , N that are connected by a communications network 918. The network 918 may be a single network or may be a variety of different networks, such as an intranet and the Internet, and may include both wire line and wireless communication channels.

In an embodiment, the entity 902 represents a service system for manufacturing collaboration, the entity 904 represents an user, such as product engineer monitoring the interested products, the entity 906 represents an engineer, such as a processing engineer to control process and the relevant recipes, or an equipment engineer to monitor or tune the conditions and setting of the processing tools, the entity 908 represents a metrology tool for IC testing and measurement, the entity 910 represents a semiconductor processing tool, the entity 912 represents a virtual metrology module associated with the processing tool 910, the entity 914 represents an advanced processing control module associated with the processing tool 910 and additionally other processing tools, and the entity 916 represents a sampling module associated with the processing tool 910.

Each entity may interact with other entities and may provide integrated circuit fabrication, processing control, and/or calculating capability to and/or receive such capabilities from the other entities. Each entity may also include one or more computer systems for performing calculations and carrying out automations. For example, the advanced processing control module of the entity 914 may include a plurality of computer hardware having software instructions encoded therein. The computer hardware may include hard drives, flash drives, CD-ROMs, RAM memory, display devices (e.g., monitors), input/output device (e.g., mouse and keyboard). The software instructions may be written in any suitable programming language and may be designed to carry out specific tasks, such as the tasks associated with optimizing the CCR values as discussed above.

The integrated circuit fabrication system 900 enables interaction among the entities for the purpose of integrated circuit (IC) manufacturing, as well as the advanced processing control of the IC manufacturing. In an embodiment, the advanced processing control includes adjusting the processing conditions, settings, and/or recipes of one processing tool applicable to the relevant wafers according to the metrology results. In another embodiment, the metrology results are measured from a subset of processed wafers according to an optimal sampling rate determined based on the process quality and/or product quality. In yet another embodiment, the metrology results are measured from chosen fields and points of the subset of processed wafers according to an optimal sampling field/point determined based on various characteristics of the process quality and/or product quality.

One of the capabilities provided by the IC fabrication system 900 may enable collaboration and information access in such areas as design, engineering, and processing, metrology, and advanced processing control. Another capability provided by the IC fabrication system 900 may integrate systems between facilities, such as between the metrology tool and the processing tool. Such integration enables facilities to coordinate their activities. For example, integrating the metrology tool and the processing tool may enable manufacturing information to be incorporated more efficiently into the fabrication process or the APC module, and may enable wafer data from the online or in site measurement with the metrology tool integrated in the associated processing tool.

Figure 10:
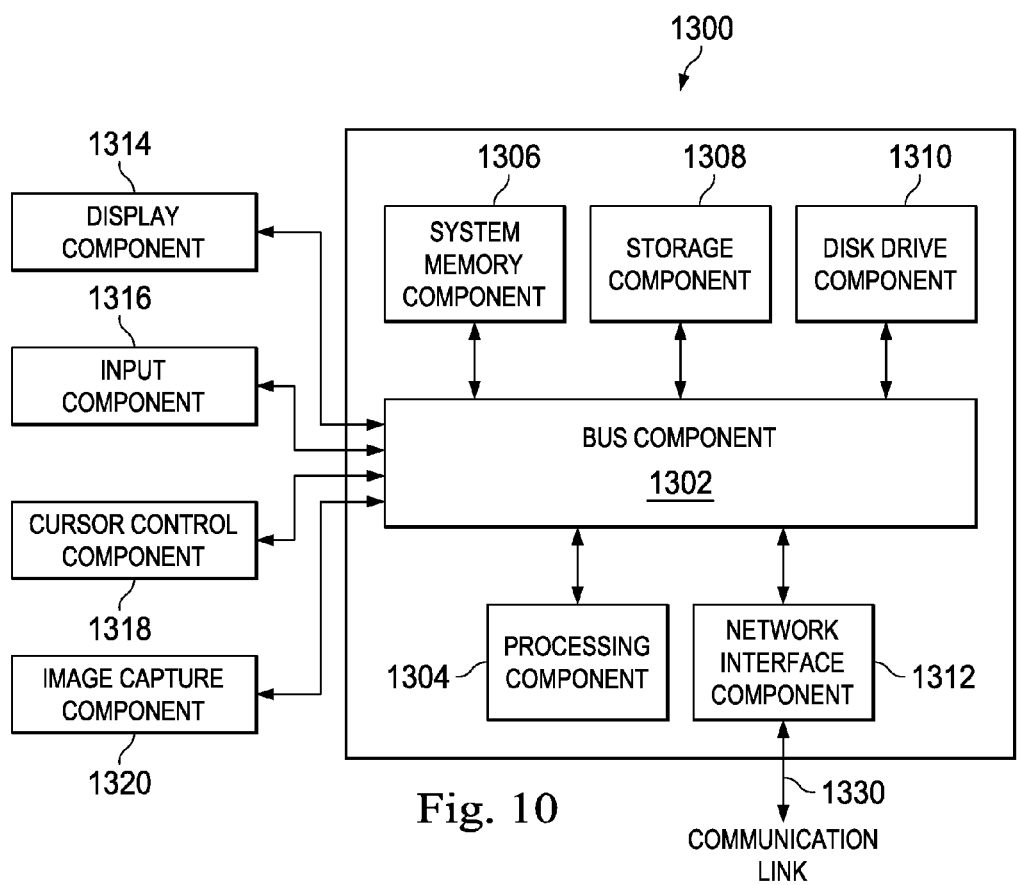
FIG. 10 illustrates a computer system capable of implementing the various methods of systematic defect extraction according to various aspects of the present disclosure.

FIG. 10 is a block diagram of a computer system 1300 suitable for implementing various methods and devices described herein, for example, the various method steps of the methods 500, 600, 700, or 800. In various embodiments, the computer system may include a tangible non-transitory computer readable medium comprising executable instructions. These executable instructions, when executed by one or more electronic processors, cause the one or more electronic processors to perform the steps of the methods 500, 600, 700, or 800. In some implementations, devices capable of performing the steps may comprise a network communications device (e.g., mobile phone, laptop, personal computer, tablet, etc.), a network computing device (e.g., a network server, a computer processor, an electronic communications interface, etc), or another suitable device. Accordingly, it should be appreciated that the devices capable of implementing the methods 500, 600, 700, or 800 may be implemented as the computer system 1300 in a manner as follows.

In accordance with various embodiments of the present disclosure, the computer system 1300, such as a network server or a mobile communications device, includes a bus component 1302 or other communication mechanisms for communicating information, which interconnects subsystems and components, such as processing component 1304 (e.g., processor, micro-controller, digital signal processor (DSP), etc.), system memory component 1306 (e.g., RAM), static storage component 1308 (e.g., ROM), disk drive component 1310 (e.g., magnetic or optical), network interface component 1312 (e.g., modem or Ethernet card), display component 1314 (e.g., cathode ray tube (CRT) or liquid crystal display (LCD)), input component 1316 (e.g., keyboard), cursor control component 1318 (e.g., mouse or trackball), and image capture component 1320 (e.g., analog or digital camera). In one implementation, disk drive component 1310 may comprise a database having one or more disk drive components.

In accordance with embodiments of the present disclosure, computer system 1300 performs specific operations by processor 1304 executing one or more sequences of one or more instructions contained in system memory component 1306. Such instructions may be read into system memory component 1306 from another computer readable medium, such as static storage component 1308 or disk drive component 1310. In other embodiments, hard-wired circuitry may be used in place of (or in combination with) software instructions to implement the present disclosure.

Logic may be encoded in a computer readable medium, which may refer to any medium that participates in providing instructions to processor 1304 for execution. Such a medium may take many forms, including but not limited to, non-volatile media and volatile media. In one embodiment, the computer readable medium is non-transitory. In various implementations, non-volatile media includes optical or magnetic disks, such as disk drive component 1310, and volatile media includes dynamic memory, such as system memory component 1306. In one aspect, data and information related to execution instructions may be transmitted to computer system 1300 via a transmission media, such as in the form of acoustic or light waves, including those generated during radio wave and infrared data communications. In various implementations, transmission media may include coaxial cables, copper wire, and fiber optics, including wires that comprise bus 1302.

Some common forms of computer readable media includes, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, carrier wave, or any other medium from which a computer is adapted to read.

In various embodiments of the present disclosure, execution of instruction sequences to practice the present disclosure may be performed by computer system 1300. In various other embodiments of the present disclosure, a plurality of computer systems 1300 coupled by communication link 1330 (e.g., a communications network, such as a LAN, WLAN, PTSN, and/or various other wired or wireless networks, including telecommunications, mobile, and cellular phone networks) may perform instruction sequences to practice the present disclosure in coordination with one another.

Computer system 1300 may transmit and receive messages, data, information and instructions, including one or more programs (i.e., application code) through communication link 1330 and communication interface 1312. Received program code may be executed by processor 1304 as received and/or stored in disk drive component 1310 or some other non-volatile storage component for execution.

Where applicable, various embodiments provided by the present disclosure may be implemented using hardware, software, or combinations of hardware and software. Also, where applicable, the various hardware components and/or software components set forth herein may be combined into composite components comprising software, hardware, and/or both without departing from the spirit of the present disclosure. Where applicable, the various hardware components and/or software components set forth herein may be separated into sub-components comprising software, hardware, or both without departing from the scope of the present disclosure. In addition, where applicable, it is contemplated that software components may be implemented as hardware components and vice-versa.

Software, in accordance with the present disclosure, such as computer program code and/or data, may be stored on one or more computer readable mediums. It is also contemplated that software identified herein may be implemented using one or more general purpose or specific purpose computers and/or computer systems, networked and/or otherwise. Where applicable, the ordering of various steps described herein may be changed, combined into composite steps, and/or separated into sub-steps to provide features described herein.

It should be appreciated that like reference numerals are used to identify like elements illustrated in one or more of the figures, wherein these labeled figures are for purposes of illustrating embodiments of the present disclosure and not for purposes of limiting the same.

One aspect of the present disclosure is directed to a method of extracting systematic wafer defects. The method includes: defining a primary area and a secondary area in a wafer layout; identifying a plurality of defects by performing a first inspection on the primary area and the secondary area for an outside-process-window wafer; performing a first nuisance defect filtering process by removing the defects in the secondary area; thereafter performing a grouping process to the defects outside the secondary area to separate the defects into a plurality of groups, wherein the defects that are grouped together have substantially similar characteristics; determining one or more groups of the defects that are associated with non-critical semiconductor features; performing a second nuisance defect filtering process by removing the one or more groups of the defects that are associated with non-critical semiconductor features; thereafter defining localized regions around remaining groups of the defects on the wafer layout; performing a second inspection on the localized regions for the outside-process-window wafer, wherein the second inspection is performed such that additional defects are identified in the localized regions in the outside-process-window wafer; thereafter performing a third inspection on the localized regions for an inside-process-window wafer, thereby identifying a plurality of potentially systematic defects; and visually examining each of the defects in the localized regions of the inside-process-window wafer to ascertain a list of systematic defects.

Another aspect of the present disclosure is directed to a method of extracting systematic wafer defects. The method includes: defining a primary area and a secondary area in a wafer layout; identifying a plurality of defects by performing a first inspection on the primary area and the secondary area for an outside-process-window wafer, wherein the first inspection is performed using a first sensitivity; removing the defects located in the secondary area; grouping the defects outside the secondary area into a plurality of groups, wherein the defects that are grouped together have substantially similar characteristics; removing one or more groups of the defects that are associated with non-critical semiconductor features; thereafter defining sensitive wafer regions around one or more groups of the defects that are associated with critical semiconductor features; performing a second inspection on the sensitive regions for the outside-process-window wafer, wherein the second inspection is performed using a second sensitivity higher than the first sensitivity such that additional defects are identified in the sensitive regions in the outside-process-window wafer; thereafter performing a third inspection on the sensitive regions for an inside-process-window wafer, thereby identifying a plurality of potentially systematic defects, wherein the potentially systematic defects constitute a subset of all the defects identified by the second inspection process; and performing a Scanning Electron Microscopy (SEM) process to determine whether the defects in the sensitive regions of the inside-process-window wafer are true systematic defects.

Yet another aspect of the present disclosure is directed to a tangible non-transitory computer readable medium comprising executable instructions that when executed by one or more electronic processors, causes the one or more electronic processors to perform the steps of: defining a primary area and a secondary area in a wafer layout; identifying a plurality of defects by performing a first inspection on the primary area and the secondary area for an outside-process-window wafer; performing a first nuisance defect filtering process by removing the defects in the secondary area; thereafter performing a grouping process to the defects outside the secondary area to separate the defects into a plurality of groups, wherein the defects that are grouped together have substantially similar characteristics; determining one or more groups of the defects that are associated with non-critical semiconductor features; performing a second nuisance defect filtering process by removing the one or more groups of the defects that are associated with non-critical semiconductor features; thereafter defining localized regions around remaining groups of the defects on the wafer layout; performing a second inspection on the localized regions for the outside-process-window wafer, wherein the second inspection is performed such that additional defects are identified in the localized regions in the outside-process-window wafer; thereafter performing a third inspection on the localized regions for an inside-process-window wafer, thereby identifying a plurality of potentially systematic defects; and visually examining each of the defects in the localized regions of the inside-process-window wafer to ascertain a list of systematic defects.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A method, comprising:
    defining a primary area and a secondary area in a wafer layout;
    identifying a plurality of defects by performing a first inspection on the primary area and the secondary area for an outside-process-window wafer;
    performing a first nuisance defect filtering process by removing the defects in the secondary area;

thereafter performing a grouping process to the defects outside the secondary area to separate the defects into a plurality of groups, wherein the defects that are grouped together have substantially similar characteristics;

determining one or more groups of the defects that are associated with non-critical semiconductor features;

performing a second nuisance defect filtering process by removing the one or more groups of the defects that are associated with non-critical semiconductor features;

thereafter defining localized regions around remaining groups of the defects on the wafer layout;

thereafter performing a second inspection on the localized regions for an inside-process-window wafer, thereby identifying a plurality of potentially systematic defects; and visually examining each of the defects in the localized regions of the inside-process-window wafer to ascertain a list of systematic defects.

2. The method of claim 1, wherein:

the primary area includes a critical layout region; and the secondary area includes a non-critical layout region.

3. The method of claim 1, wherein the grouping process comprises at least one of: a pattern grouping process or a feature grouping process.

4. The method of claim 1, wherein the grouping process is performed using a field of view (FOV) less than about 1 micron.

5. The method of claim 1, wherein the second inspection is performed using a higher sensitivity than the first inspection.

6. The method of claim 1, wherein at least one of the following method steps is performed via one or more electronic processors: the defining the primary area and the secondary area, the identifying, the performing the first nuisance defect filtering process, the performing the grouping process, the determining, the performing the second nuisance defect filtering process, the defining the localized regions, the performing the second inspection process, and the visually examining.

7. The method of claim 1, wherein the visually examining is performed at least in part using a Scanning Electron Microscopy (SEM) machine.

8. The method of claim 1, further comprising: modifying at least one of: a photomask design or a circuit design in response to the systematic defects.

9. A method, comprising:

defining a primary area and a secondary area in a wafer layout;

identifying a plurality of defects by performing a first inspection on the primary area and the secondary area for an outside-process-window wafer, wherein the first inspection is performed using a first sensitivity;

removing the defects located in the secondary area;

grouping the defects outside the secondary area into a plurality of groups, wherein the defects that are grouped together have substantially similar characteristics;

removing one or more groups of the defects that are associated with non-critical semiconductor features;

thereafter defining sensitive wafer regions around one or more groups of the defects that are associated with critical semiconductor features;

thereafter performing a second inspection on the sensitive regions for an inside-process-window wafer, thereby identifying a plurality of potentially systematic defects; and performing a Scanning Electron Microscopy (SEM) process to determine whether the defects in the sensitive regions of the inside-process-window wafer are true systematic defects.

10. The method of claim 9, wherein:

the primary area includes a critical layout region; and the secondary area includes a non-critical layout region.

11. The method of claim 9, wherein the grouping process comprises at least one of: a pattern grouping process or a feature grouping process.

12. The method of claim 9, wherein the grouping is performed using a field of view (FOV) less than about 1 micron.

13. The method of claim 9, further comprising: revising at least one of: a photomask design or a circuit design so as to reduce or eliminate the true systematic defects for future wafers.

14. A tangible non-transitory computer readable medium comprising executable instructions that when executed by one or more electronic processors, causes the one or more electronic processors to perform the steps of:

defining a primary area and a secondary area in a wafer layout;

identifying a plurality of defects by performing a first inspection on the primary area and the secondary area for an outside-process-window wafer;

performing a first nuisance defect filtering process by removing the defects in the secondary area;

thereafter performing a grouping process to the defects outside the secondary area to separate the defects into a plurality of groups, wherein the defects that are grouped together have substantially similar characteristics;

determining one or more groups of the defects that are associated with non-critical semiconductor features;

performing a second nuisance defect filtering process by removing the one or more groups of the defects that are associated with non-critical semiconductor features;

thereafter defining localized regions around remaining groups of the defects on the wafer layout;

thereafter performing a second inspection on the localized regions for an inside-process-window wafer, thereby identifying a plurality of potentially systematic defects; and visually examining each of the defects in the localized regions of the inside-process-window wafer to ascertain a list of systematic defects.

15. The tangible non-transitory computer readable medium of claim 14, wherein:

the primary area includes a critical layout region; and the secondary area includes a non-critical layout region.

16. The tangible non-transitory computer readable medium of claim 14, wherein the grouping process comprises at least one of: a pattern grouping process or a feature grouping process.

17. The tangible non-transitory computer readable medium of claim 14, wherein the grouping process is performed using a field of view (FOV) less than about 1 micron.

18. The tangible non-transitory computer readable medium of claim 14, wherein the second inspection is performed using a higher sensitivity than the first inspection.

19. The tangible non-transitory computer readable medium of claim 14, wherein the instructions, when executed by one or more electronic processors, further causes the one or more electronic processors to perform a step of: modifying a photomask design or a circuit design in response to the list of systematic defects.

20. The tangible non-transitory computer readable medium of claim 14, wherein:

the first second inspection are each performed at least in part using a wafer inspection tool;
the visually examining is performed at least in part using a Scanning Electron Microscopy (SEM) tool; and
at least the first and second nuisance filtering process are performed at least in part using a hot spot analyzer tool.

* * * * *